US012570674B2

(12) United States Patent
Liu et al.

(10) Patent No.: US 12,570,674 B2
(45) Date of Patent: Mar. 10, 2026

(54) BORON CARRYING AGENT FOR INTEGRATED TUMOR DIAGNOSIS AND TREATMENT, AND PREPARATION METHOD THEREFOR AND USE THEREOF

(71) Applicant: Peking University, Beijing (CN)

(72) Inventors: Zhibo Liu, Beijing (CN); Junyi Chen, Beijing (CN)

(73) Assignee: Peking University, Beijing (CN)

( * ) Notice: Subject to any disclaimer, the term of this patent is extended or adjusted under 35 U.S.C. 154(b) by 856 days.

(21) Appl. No.: 17/908,630

(22) PCT Filed: Mar. 1, 2021

(86) PCT No.: PCT/CN2021/078438
§ 371 (c)(1),
(2) Date: Sep. 1, 2022

(87) PCT Pub. No.: WO2021/175183
PCT Pub. Date: Sep. 10, 2021

(65) Prior Publication Data
US 2023/0312611 A1        Oct. 5, 2023

(30) Foreign Application Priority Data

Mar. 3, 2020    (CN) ......................... 202010137553.7

(51) Int. Cl.
| *A61P 35/00* | (2006.01) |
| *A61K 41/00* | (2020.01) |
| *A61K 51/04* | (2006.01) |
| *C07F 5/02* | (2006.01) |

(52) U.S. Cl.
CPC .......... *C07F 5/025* (2013.01); *A61K 41/0095* (2013.01); *A61K 51/04* (2013.01); *A61P 35/00* (2018.01); *C07B 2200/05* (2013.01)

(58) Field of Classification Search
CPC .......... C07F 5/025; A61P 35/00; A61K 51/04
See application file for complete search history.

(56) References Cited

U.S. PATENT DOCUMENTS 10,344,042 B2 * 7/2019 Takenaka .............. C07C 229/36
2016/0311836 A1 10/2016 Takenaka et al.

FOREIGN PATENT DOCUMENTS

| CN | 108299482 A | 7/2018 |
| CN | 109053781 A | 12/2018 |
| CN | 109384806 A | 2/2019 |
| CN | 109776587 A | 5/2019 |
| CN | 110835352 A | 2/2020 |

OTHER PUBLICATIONS

Laura Evangelista et al., "Boron neutron capture therapy and 18F-labelled borophenylalanine positron emission tomography: A critical and clinical overview of the literature", Applied Radiation and Isotopes, vol. 74, Jan. 11, 2013, 91-101.
International Search Report and Written Opinion from PCT/CN2021/078438 dated Jun. 7, 2021.

* cited by examiner

*Primary Examiner* — Michael G. Hartley
*Assistant Examiner* — Jagadishwar R Samala
(74) *Attorney, Agent, or Firm* — Blank Rome LLP

(57)        ABSTRACT

The present invention relates to a boron carrying agent for integrated tumor diagnosis and treatment, and a preparation method therefor and use thereof. Provided is a compound represented by formula I: wherein an R group is hydrogen or alkyl. A boron atom connected to the benzene ring may be 10B or natural boron, and at least one fluorine atom in —BF 3- is radiolabeled. The present invention generally relates to the fields of radiopharmaceuticals and nuclear medicine. The compound in the present invention can be used for a drug for integrated diagnosis and treatment in tumor diagnosis and BNCT treatment, and by means of the same chemical structure, a reliable distribution result of a drug in vivo is provided.

14 Claims, 10 Drawing Sheets

BORON CARRYING AGENT FOR INTEGRATED TUMOR DIAGNOSIS AND TREATMENT, AND PREPARATION METHOD THEREFOR AND USE THEREOF

CROSS-REFERENCE TO RELATED APPLICATIONS

This application is a National Stage of International Patent Application No. PCT/CN2021/078438, filed Jan. 3, 2021, which claims the priority of Chinese Patent Application No. CN 202010137553.7, filed Mar. 3, 2020, the entire contents of which are hereby incorporated by reference in their entirety.

TECHNICAL FIELD

The present application generally relates to the fields of radiopharmaceuticals and nuclear medicine, and particularly relates to a boron carrying agent for integrated tumor diagnosis and treatment, which is used for boron neutron capture therapy and tumor diagnosis.

BACKGROUND

Boron neutron capture therapy (BNCT) is a binary targeted radiation precision medical technology. A patient is first administered a boron-carrying agent drug that can accumulate in tumor cells, and then the patient is irradiated with thermal neutrons or epithermal neutrons. The principle is to apply highly targeted boron-containing drugs to patients and generate enrichment in cancer cells. The capture cross section of 10B for thermal neutrons is very high compared to the normal elements of human body composition. The capture reaction between thermal neutrons and 10B atoms makes the energy of high-energy a particles and Li particles generated only act on cancer cells of about 10 μm, causing irreversible damages to the structure of the cells, making them irreparable and apoptosis. The use of this therapy for malignant tumor treatment can kill tumor tissue while preserving surrounding normal tissue and function to the greatest extent, so as to improve the quality of life and survival period of patients after treatment. 4-Boronic acid-L-phenylalanine (4-L-boronophenylalanine, BPA) is the most commonly used boron carrier drug for BNCT approved by FDA. However, since the treatment strategies for BNCT need to be planned based on the pharmacokinetic results of boron-carrying agents, how to effectively obtain the concentrations of BPA in tumors and other tissues and organs has become one of the key issues in various studies.

Positron Emission Tomography (PET) is a molecular imaging technology based on radioactive molecular probes, which combines molecular probes and medical imaging technology, and is able to conduct qualitative and quantitative studies on in vivo pathological and physiological processes at the cellular and molecular levels. The positron-bearing electrons emitted from positron-decaying isotopes such as 11C and 18F quickly annihilate with surrounding widely-distributed negative-bearing electrons, which converts energy into two photons with energy of 511 keV in opposite directions. The two photons are simultaneously detected by opposite two probes of the instrument, indicating that an annihilation has occurred on the line connecting the two probes. In this way, PET can accurately locate and quantify the distribution of radioactivity in the body. With computer reconstruction, a three-dimensional PET image of the human body can be obtained. PET is one of the most effective means to study drug distribution in vivo.

Combining treatment components on the basis of PET imaging to realize the integration of tumor imaging and treatment is the direction of technological development. 2-fluoro-4-L-boronophenylalanine (FBPA) is a BPA substituted with a fluorine atom at the second position on the benzene ring. This fluorine atom may be radioactive 18F, in which case the molecule can act as a PET probe to simulate the distribution of BPA in the body. PET imaging technology using [$^{18}$F]-FBPA as a probe has now been applied to the pre-treatment diagnosis of BNCT, which helps to understand the dynamic distribution of BPA in patients (Ishiwata K, et al. Melanoma Research, 1992. PMID: 1450671). However, there are differences in molecular structure between FBPA and BPA, the probe dose of FBPA cannot represent the distribution of therapeutic dose of BPA in the body, and the FBPA-PET technology is not mature, so it is urgent to develop a novel drug molecule that can realize the integration of diagnosis and treatment.

SUMMARY OF THE INVENTION

BNCT therapy must rely on the high enrichment of the boron-carrying agent at the tumor site, and a treatment plan is customized according to its enrichment, which requires real-time monitoring of the in vivo concentration distribution of the boron-carrying agent. It is particularly important to study the distribution of BPA, which is the only approved BNCT drug at present, in the body. One important method is to obtain [$^{18}$F]FBPA by introducing radioactive $^{18}$F on the benzene ring of BPA by means of PET molecular imaging. The distribution of BPA in vivo is simulated with [$^{18}$F] FBPA, and then BNCT is planned. However, it is difficult to ensure that the chemical and biological properties of [$^{18}$F] FBPA are still the same as those of BPA when a H atom on the benzene ring is replaced with an F atom in chemical structure, and this difference will bring greater uncertainty to BNCT.

BPA

[$^{18}$F]FBPA

Aiming at the problem that the existing FBPA-PET cannot accurately and effectively reflect the distribution of BPA in the body and realize BNCT accurately and efficiently, the present application provides a novel boron-carrying agent BF$_3$-BPA for integrated diagnosis and treatment, which can be radiolabeled easily, has the same chemical structure before and after being labeled, and can accurately reflect its distribution in the body, so as to solve the problem of unclear prediction of the real-time distribution of conventional boron-carrying agents in the body; and the boron-carrying agent can achieve more efficient BNCT by providing two boron atoms in the molecule.

[$^{18}$F]FB$_3$-BPA

The concept of the present disclosure lies in that: boronic acid is an amino acid derivative formed by replacing the carboxyl group of a natural amino acid with boron trifluoride. Boronic acid may construct a radioactive probe by being radiolabeled with 18F through 18F-19F isotope exchange reaction, thereby realizing PET imaging. The inventors have found in the study that the boron trifluoride group shows a high level of similarity with the carboxylate group in electrical properties, so boronine also shows similarities with its corresponding natural amino acid in biological recognition and transport. Based on this, the applicant has found that BF$_3$-BPA may be constructed by replacing the carboxyl group in BPA with a boron trifluoride group, and it may be highly enriched in tumor areas. On the one hand, BF$_3$-BPA may be labeled with F-18 to achieve molecular concentration distribution analysis in the body; and on the other hand, it may also be directly used as a boron-carrier agent for BNCT, and since BF$_3$-BPA has a completely identical chemical structure before and after being radiolabeled, the distribution of BF$_3$-BPA in the body can be accurately reflected by [$^{18}$F]BF$_3$-BPA, which provides an important basis for the implementation of BNCT therapy. More importantly, with two boron atoms, BF$_3$-BPA has a stronger carrying capacity of boron element and achieves more efficient delivery of boron element.

Since an intermediate with two boronic acid groups is produced during the preparation process of the molecule of the present disclosure, if trifluoroboration is carried out at the wrong position, the negative charge of the trifluoroborate will seriously affect the chemical and pharmaceutical properties of the molecule, and finally affect its efficacy. In the process of synthesizing BF$_3$-BPA, selective trifluoroboration of the α-amino boronic acid group is desired, and trifluoroboration of the aromatic ring is to be avoided. Due to the differences in chemical properties between the benzene ring and the α-amino group, the aromatic boron trifluoride group will be preferentially generated during the fluorination process, and thus the desired trifluoroboration product BF$_3$-BPA cannot be obtained. During the study of the synthesis process, the applicant has found that the hydrolysis rate of the α-amino boron trifluoride group is different from that of the aromatic boron trifluoride group, and the latter is $10^2$-$10^3$ times higher than the former, which makes it possible to synthesize BF$_3$-BPA. The present application also provides a novel method of preparing BF$_3$-BPA, comprising obtaining an intermediate containing double boron trifluoride groups under general trifluoroboration conditions, and then performing hydrolysis under hydrolysis conditions to hydrolyze the boron trifluoride group attached to the benzene ring to obtain the target product of BF$_3$-BPA.

In one aspect, the present application provides a compound of Formula I:

Formula I wherein R group is hydrogen or alkyl.

In one embodiment, the boron atom attached to the benzene ring is $^{10}$B or natural boron. In one embodiment, at least one of the fluorine atoms in —BF$_3^-$ is radiolabeled.

In one embodiment, the alkyl group is methyl.

In one embodiment, the boron atom in —BF$_3^-$ is natural boron.

In another aspect, the present application provides a composition of a boron-carrying agent comprising one or more compounds of Formula I of the present application and a pharmaceutically acceptable carrier.

In one embodiment, the composition of the boron-carrying agent further comprises one or more of fructose, disodium mercaptoundecahydrododecaborate and dimers thereof, boronated dendrimer-EGF bioconjugates, EGFR monoclonal antibody-borate conjugates, FR-targeted boron-containing liposomes, FR-targeted boron-containing nanoparticles, and borate porphyrins.

In another aspect, the present application provides a method of preparing the compound of the invention, comprising the steps of: producing an intermediate containing double boron trifluoride groups by adding KHF$_2$ solution to compound 7 and adding hydrochloric acid to reach an acidity of pH<0; and then increasing the acidity to pH of 1.5 to 4, preferably pH of 2 to 2.5 to obtain the compound of the present application.

In one embodiment, compound 7 is obtained by adding NaOH solution to compound 6

6 to achieve a final concentration of 0.4-0.6 M, stirring the solution at room temperature for 20-40 minutes, and then adding concentrated hydrochloric acid for neutralization.

In one embodiment, the preparation method comprises a step of obtaining compound 3

3 by adding N-methyliminoacetic acid to compound 2

2

In one embodiment, the preparation method comprises the steps of:

(1) converting p-bromobenzene ethanol

1 to compound 2

2

(2) converting compound 2 to compound 3

3 with the addition of N-methyliminoacetic acid;

(3) converting compound 3 to compound 4

4

(4) converting compound 4 to compound 5

5

(5) converting compound 5 to compound 6

6

(6) converting compound 7 to compound 8

8(BF$_3$-BPA)

and (7) optionally converting compound 8 to

[$^{18}$F]BF$_3$-BPA

7

In yet another aspect, the present application provides the use of the compound of the present application in the manufacture of a medicament for treatment or diagnosis of cancer.

In one embodiment, the medicament is a boron-carrying agent for integrated tumor diagnosis and treatment or boron neutron capture therapy.

In one embodiment, the cancer is selected from squamous cell carcinoma, lung cancer, peritoneal cancer, hepatocellular carcinoma, gastric cancer, melanoma, pancreatic cancer, glioblastoma, cervical cancer, ovarian cancer, liver cancer, bladder cancer, hepatic tumor, breast cancer, colon cancer, colorectal cancer, uterine cancer, salivary gland cancer, kidney cancer, liver cancer, prostate cancer, vulvar cancer, thyroid cancer, liver cancer, head and neck cancer, B-cell lymphoma or leukemia.

The advantages of the present disclosure are as follows:

(1) the present disclosure uses $BF_3$-BPA having the same chemical structure before and after being labeled with $^{18}F$ and $[^{18}F]BF3$-BPA, which may be used for the drug for integrated tumor diagnosis and BNCT treatment, and provides reliable drug distribution results in the body due to the same chemical structure;

8(BF₃-BPA)

[¹⁸F]BF₃-BPA (2) it has higher B delivery efficiency due to the two B atoms in the structure;

(3) the method of the present disclosure achieves the fluorination of a single boron;

(4) the compounds of the present disclosure have high uptake in tumors;

(5) the present application provides a novel boron-carrying agent $BF_3$-BPA for integrated diagnosis and treatment, which is used for treatment planning before BNCT by obtaining the dynamic distribution of the boron-carrying agent, and can also be directly used for BNCT; and (6) the present application provides a novel method of preparing the compound of the present application.

8

Figure 5:
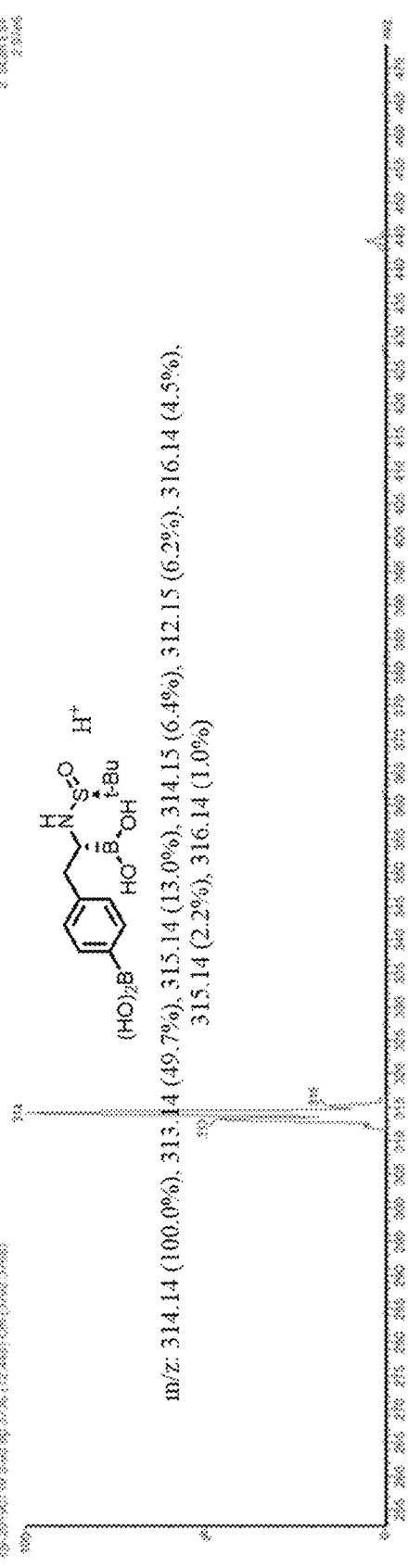

FIG. 5: HPLC-MS [M–H]⁻ mass spectrometry results of compound 7.

Figure 6:
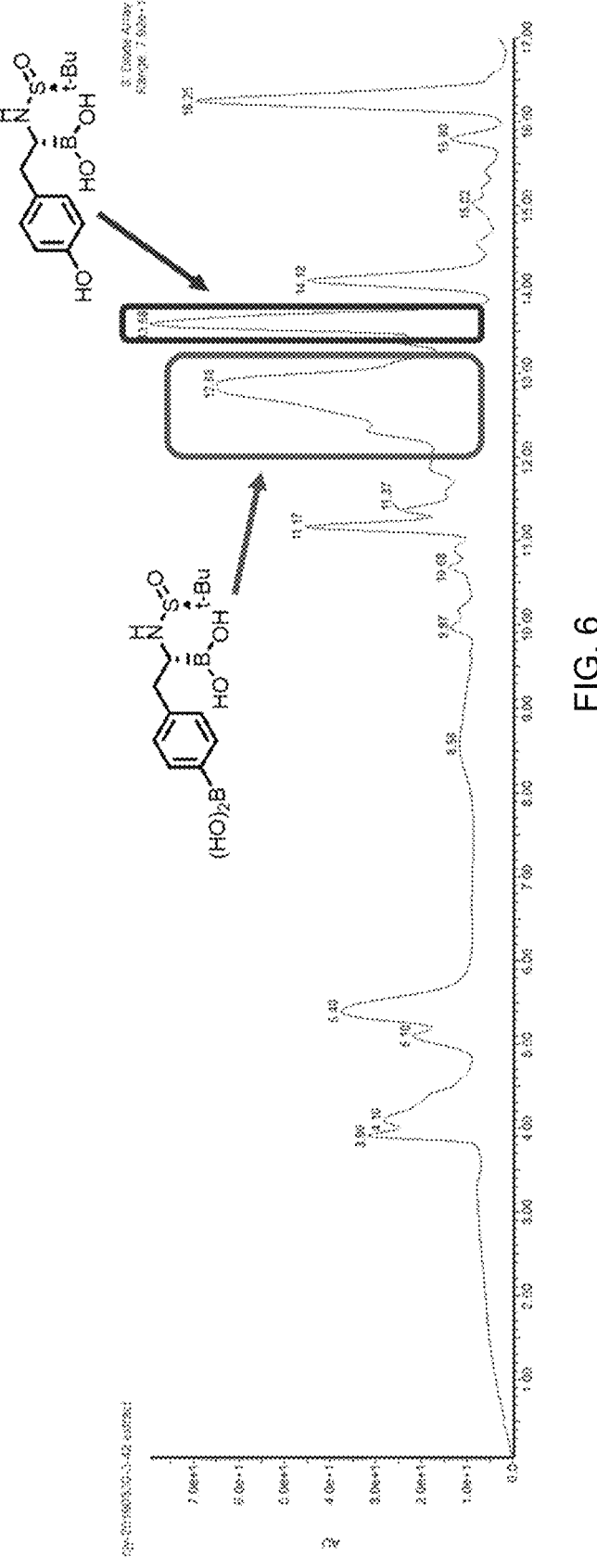

FIG. 6: High performance liquid chromatogram of compound 7 and by-products.

Figure 7:
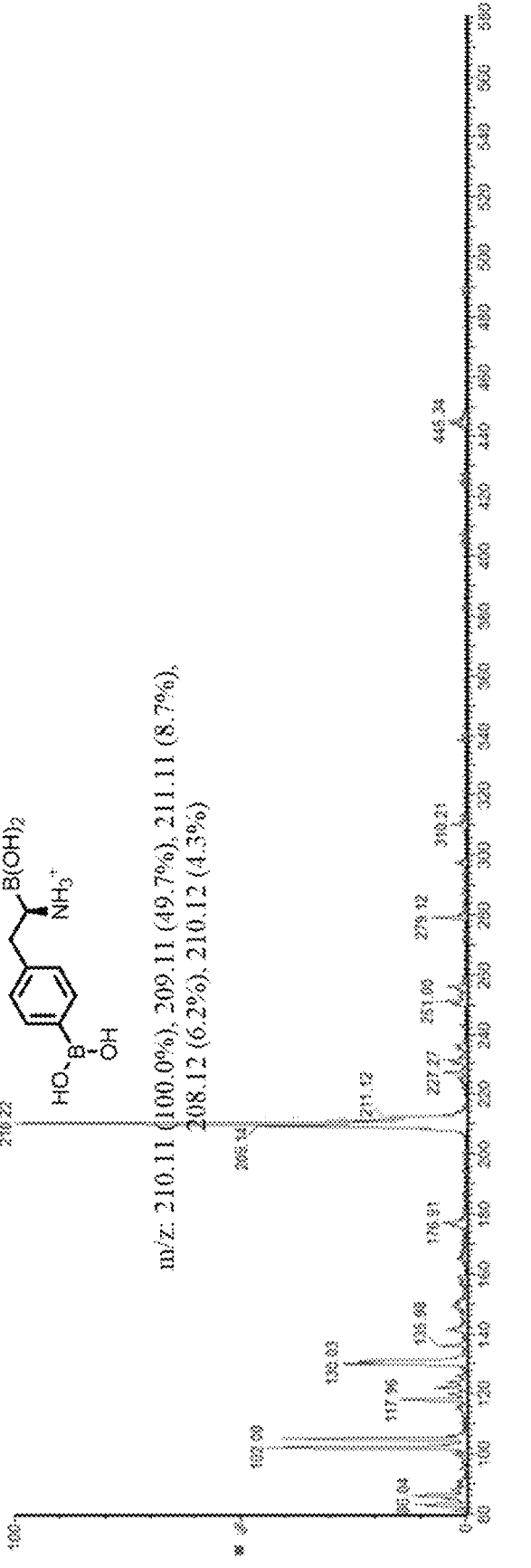

FIG. 7: HPLC-MS [M+H]⁺ mass spectrum of compound 10.

Figure 8:
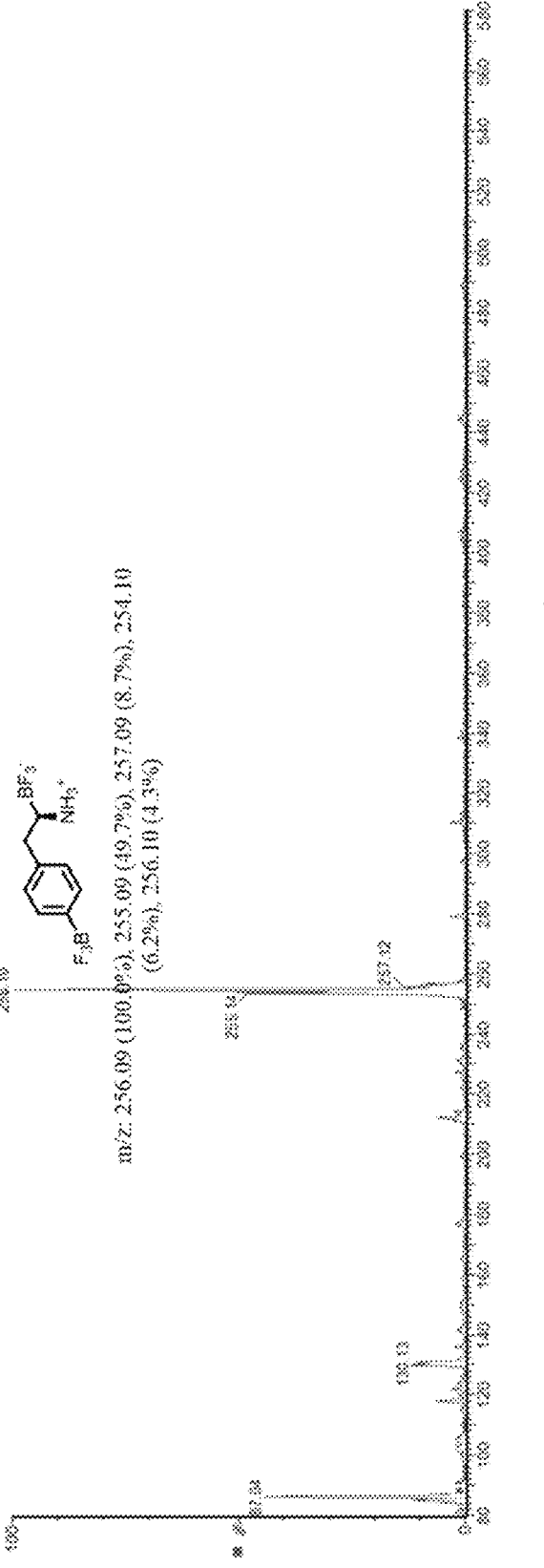

FIG. 8: HPLC-MS [M–H]⁻ mass spectrum of compound 11.

Figure 9:
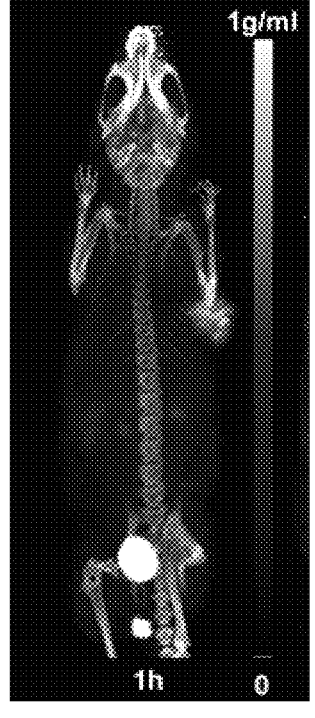

FIG. 9: Small animal PET/CT imaging of $[^{18}F]BF_3$-BPA injected in the tail vein of a tumor-bearing mouse.

Figure 10:
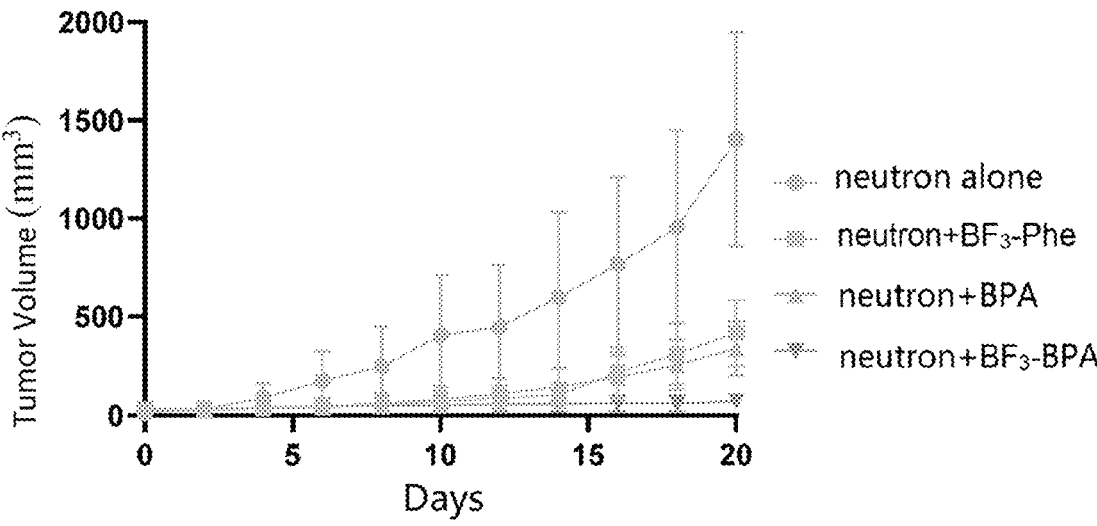

FIG. 10: The tumor growth curve of $BF_3$-BPA for BNCT tumor therapy.

DETAILED DESCRIPTION

The present application provides a compound of Formula I:

Formula I

In formula (I), R is independently hydrogen or alkyl. "Alkyl" refers to a saturated linear hydrocarbon group. For example, alkyl may be methyl, ethyl, propyl, butyl, pentyl, and the like. Preferably, the R group is methyl.

In formula (I), at least one of the fluorine atoms in —$BF_3^-$ is radiolabeled. For example, 1, 2 or 3 fluorine atoms are $^{18}F$. The boron atom in —$BF_3^-$ may be natural boron.

In formula (I), the boron atom attached to the benzene ring is $^{10}B$ or natural boron.

The present application further provides a composition of a boron-carrying agent comprising the compound of the present application and a pharmaceutically acceptable carrier. The composition of the boron-carrying agent further comprises fructose or other boron-carrying agent(s), such as one or more of disodium mercaptoundecahydrododecaborate and dimers thereof, boronated dendrimer-EGF bioconjugates, EGFR monoclonal antibody-borate conjugates, FR-targeted boron-containing liposomes, FR-targeted boron-containing nanoparticles, and borate porphyrins.

The preparation method of the present application comprises the steps of:

(1) adding $PCy_3 \cdot HBF_4$ to toluene, followed by adding $CuSO_4 \cdot 5H_2O$ solution and deionized water, and stirring vigorously at room temperature, and then adding benzylamine under nitrogen protection to form a dark blue catalyst; adding toluene, followed by adding compound 5 and B2pin2; subsequently, the reaction system undergoes reaction at room temperature until the reactants are consumed completely; adding saturated EDTA to wash the reaction mixture, and then washing the mixture with saturated brine; combining the organic phases and then drying it over anhydrous $Na_2SO_4$, and removing the organic solvent in vacuo to obtain a yellow oil liquid; and (2) dissolving the product in acetonitrile, adding NaOH solution, stirring the mixture at room temperature, and then adding concentrated hydrochloric acid for neutralization to obtain a reaction mixture;

(3) adding $KHF_2$ solution to the reaction mixture, then adding concentrated hydrochloric acid dropwise until pH<0, and reacting at room temperature for 2 hours; removing HCl through evaporation under reduced pressure to reduce the acidity to pH of 2, reacting for 30 min, adding acetonitrile and azeotropic drying, extraction washing the solid with acetonitrile, discarding the insolubles, and purifying the acetonitrile phase to obtain compound 8: $BF_3$-BPA:

Compound 8

BF₃-BPA

Figure 1:
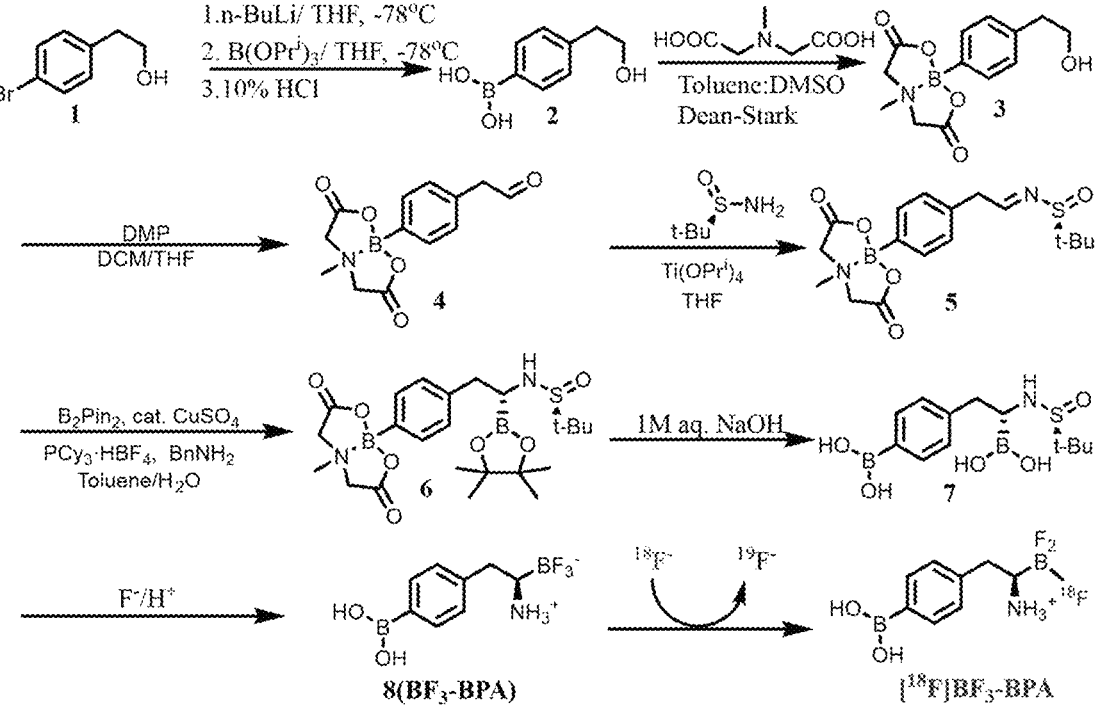
FIG. 1: synthetic route of $BF_3$-BPA and $[^{18}F]BF_3$-BPA.
Figure 2A:
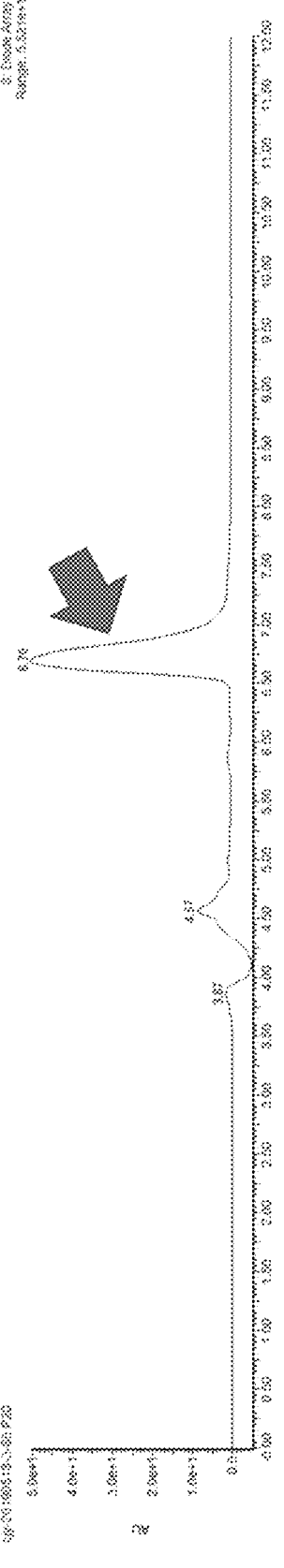
FIGS. 2A-2B: the HPLC-MS results of compound 8 ($BF_3$-BPA).
Figure 2B:
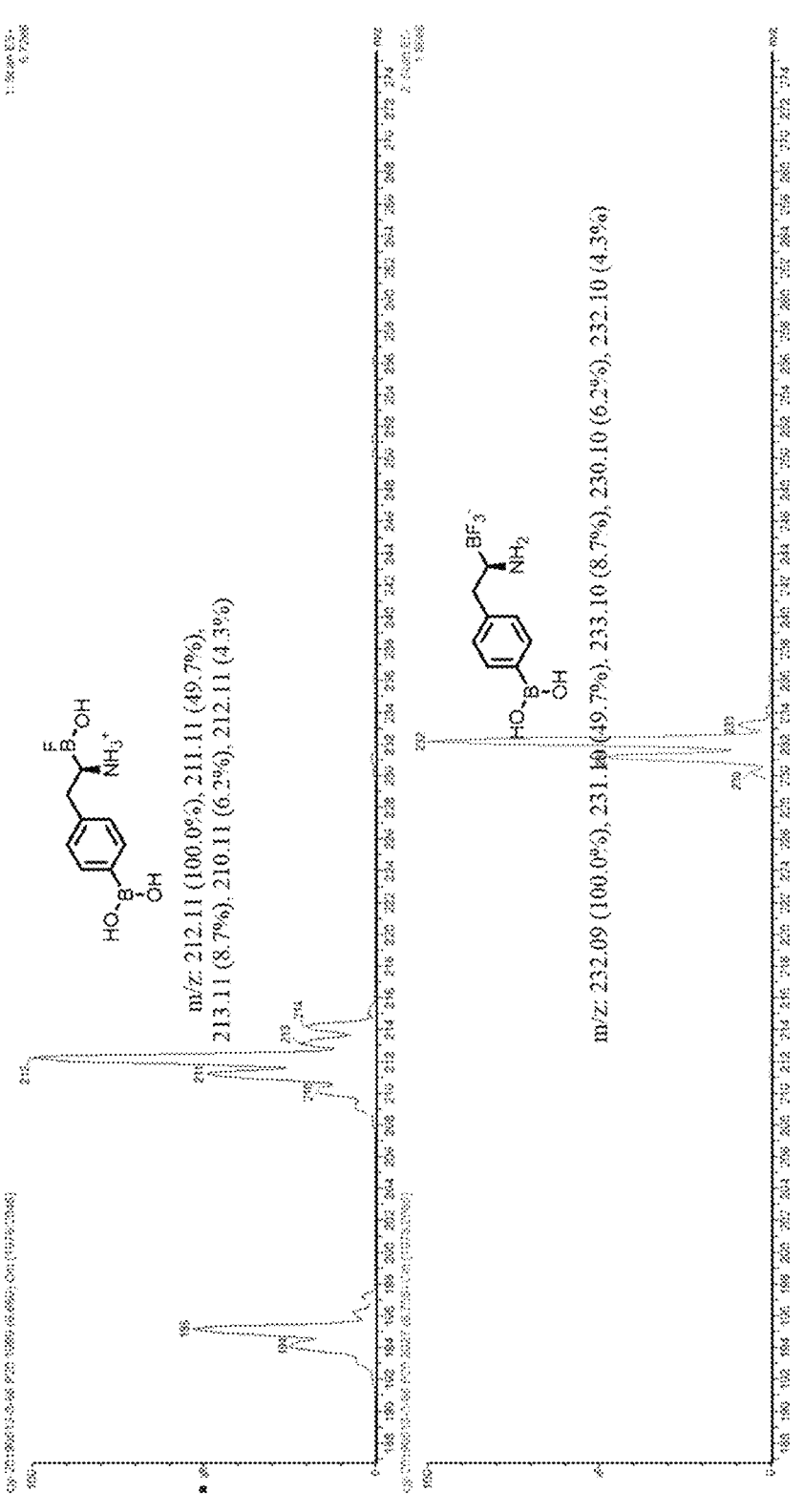
Figure 3:
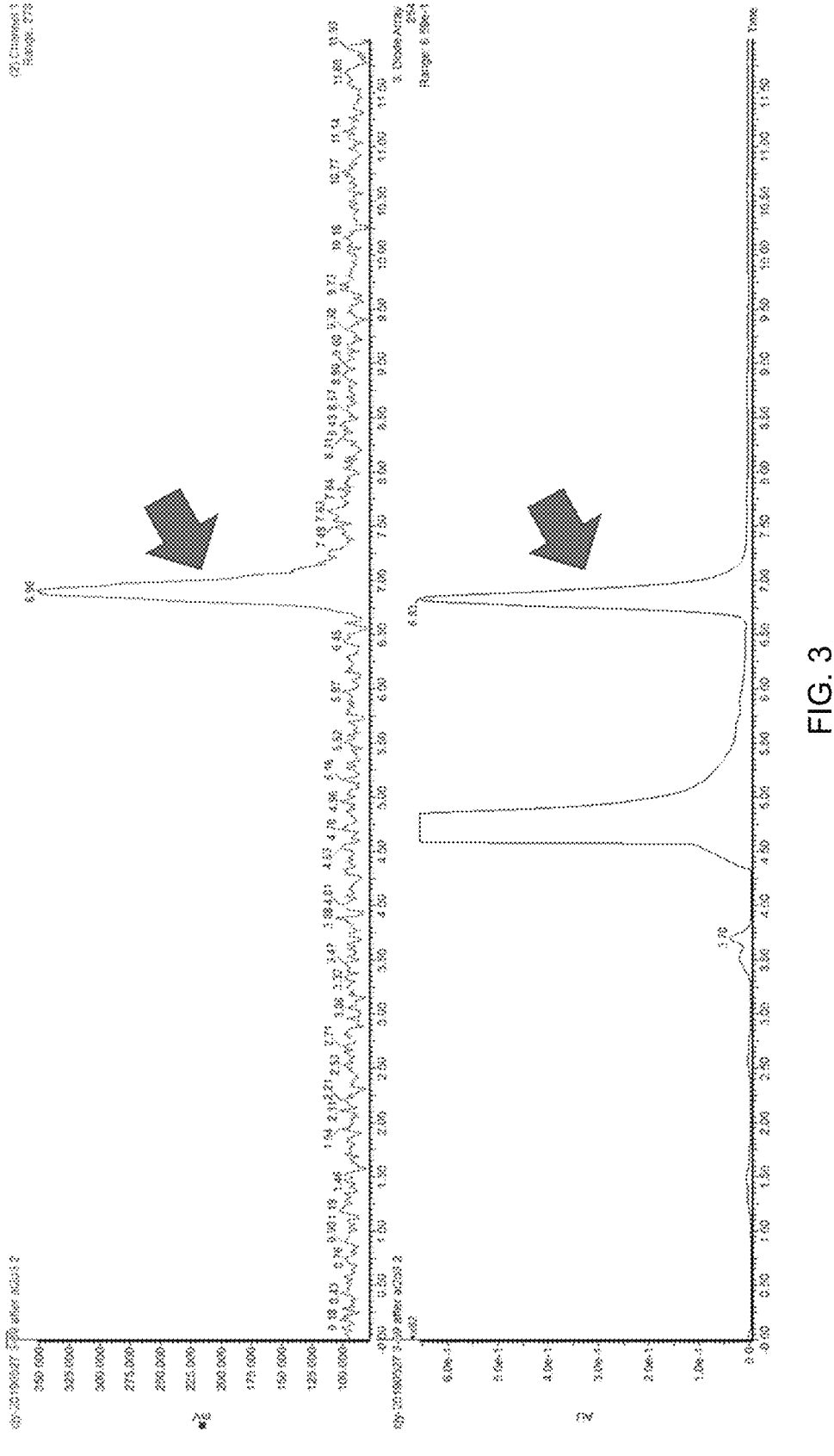
FIG. 3: $[^{18}F]BF_3$-BPA radio-HPLC results.

The preparation method of the present application is shown in FIG. 1 and comprises the steps of:

dissolving p-bromophenethyl alcohol (compound 1) in anhydrous tetrahydrofuran, cooling the solution to −90° C. to −70° C. (e.g., −78° C.), adding n-butyllithium/hexane solution dropwise, the solution gradually turns yellow and then becomes off-white paste, keep stirring at −90° C. to −70° C. (e.g., −78° C.) (e.g., for 15 min); then adding triisopropyl borate dropwise, the solution becomes clear, and reacting at −90° C. to −70° C. (e.g., −78° C.) (e.g., for 20 min); raising the temperature to room temperature, adding hydrochloric acid and stirring the mixture at room temperature (e.g., for 15 min); separating the liquids, extracting the aqueous phase with ethyl acetate, combining the organic phases, washing it with saturated sodium chloride, drying it over anhydrous sodium sulfate, and removing the solvent in vacuo to obtain compound 2 as a white solid; the compound is used directly in the next reaction without further purification; compound 2: 1H NMR (400 MHz, Methanol-d4) δ 7.60-6.94 (m, 4H), 3.75 (t, J=7.1 Hz, 2H), 2.82 (t, J=7.1 Hz, 2H);

dissolving compound 2 in toluene, adding DMSO, followed by adding N-methyliminoacetic acid; refluxing, and setting up a water separator filled with toluene, and the reaction is completed after about 2 hours (e.g., 1.5-3 hours); removing the organic solvent in vacuo and separating the product using silica gel column chromatography to obtain compound 3 as white crystals; compound 3: 1H NMR (400 MHz, Methanol-d4) δ7.53-7.10 (m, 4H), 4.35-3.96 (m, 4H), 3.75 (t, J=7.0 Hz, 2H), 3.31 (s, 3H), 2.82 (t, J=7.1 Hz, 2H), dissolving compound 3 in a mixed solvent of anhydrous dichloromethane and anhydrous tetrahydrofuran, adding DMP oxidant, and then adding sodium bicarbonate powder; reacting at room temperature (e.g., for 1 hour); adding saturated sodium thiosulfate solution and saturated sodium bicarbonate solution and stirring (e.g., for 15 minutes); removing the insolubles by filtration, separating the organic phase, extracting the aqueous phase with ethyl acetate, combining the organic phases, washing it with saturated sodium chloride (e.g., 30 ml×2), drying it over anhydrous sodium sulfate, and removing the solvent in vacuo; and separating the product with silica gel column chromatography to obtain compound 4 as a white solid; compound 4: 1H NMR (400 MHz, Acetone-d6) δ 9.74 (s, 1H), 7.41 (dd, J=100.7, 7.9 Hz, 4H), 4.48-4.07 (m, 4H), 2.75 (s, 3H);

dissolving compound 4 in anhydrous tetrahydrofuran, adding tert-butylsulfinamide, adding tetraethyl titanate dropwise, and stirring the mixture at room temperature (e.g., for 2 hours); adding water to quench the reaction and stirring the mixture, filtering the mixture to remove the insolubles, separating the organic phase, extracting the aqueous phase with ethyl acetate (e.g., 20 ml×3), combining the organic phases, washing it with saturated sodium chloride (e.g., 30 ml×2), drying it over anhydrous sodium sulfate and removing the solvent in vacuo; separating the product, for example, by silica gel column chromatography to obtain compound 5 (490 mg, 66%) as yellow crystals; compound 5: 1H NMR (400 MHz, Acetone-d6) δ 8.07 (s, 1H), 7.43 (dd, J=83.2, 7.9 Hz, 4H), 4.51-4.03 (m, 4H), 3.91 (d, J=5.1 Hz, 2H), 2.73 (s, 3H), 1.12 (s, 9H);

adding $PCy_3$·$HBF_4$ to toluene, followed by adding $CuSO_4$·$5H_2O$ solution and deionized water, and stirring vigorously at room temperature, and then adding benzylamine under nitrogen protection to form a dark blue catalyst; adding toluene, keeping the reaction system at 0-4° C. (e.g., 0° C.), adding compound 5 and B2pin2; subsequently, raising the temperature of the reaction system to room temperature, reacting (e.g., for 1 hour) until TLC shows that the reactants are consumed completely; adding saturated EDTA to wash the reaction mixture, and then washing the mixture with saturated brine; combining the organic phases, then drying it over anhydrous $Na_2SO_4$, and removing the organic solvent in vacuo to obtain compound 6 as a yellow oil liquid; and the crude product is used directly in the next reaction without purification;

dissolving compound 6 in acetonitrile, adding NaOH solution, stirring the mixture (e.g., at room temperature for half an hour), and then adding concentrated hydrochloric acid for neutralization to obtain a reaction mixture containing compound 7 which is directly used for the next reaction;

adding $KHF_2$ solution to the reaction mixture containing compound 7, then adding 4.7 ml of concentrated hydrochloric acid dropwise until pH<0, and reacting at room temperature for 2 hours; removing HCl through evaporation under reduced pressure to reduce the acidity to pH of 2, reacting for 30 min, adding acetonitrile and azeotropic drying, extraction washing the solid with acetonitrile, discarding the insolubles, and purifying the acetonitrile phase (e.g., using pre-HPLC) to obtain $BF_3$-BPA (compound 8); and the HPLC-MS results are shown in FIG. 2B; and dissolving $BF_3$-BPA (compound 8) in DMF, then adding pyridazine-HCl buffer, and then adding 18F-labeled water-aqueous solution; the reaction mixture is reacted, for example, at 85° C. for 15 min, then quenching the reaction with normal saline, and removing free fluoride ions (e.g., using a Sep-Pak Alumina Light cartridge) to obtain the final product [$^{18}F$]$BF_3$-BPA; and the Radio-HPLC results are shown in FIG. 3.

The present application provides the use of the compound of the boron-carrying agent in the manufacture of a medicament for treatment or diagnosis of cancer. The medicament may be a boron-carrying agent for integrated tumor diagnosis and treatment or boron neutron capture therapy.

The terms "cancer" and "cancerous" refer to or describe the physiological condition in mammals that is often characterized by unregulated cell growth. Examples of cancer include, but are not limited to, carcinoma, lymphoma, blastoma, sarcoma, and leukemia. More specific examples of such cancer include squamous cell carcinoma, lung cancer (including small cell lung cancer, non-small cell lung cancer, lung adenocarcinoma, and lung squamous cell carcinoma), peritoneal cancer, hepatocellular carcinoma, gastric cancer (including gastrointestinal cancer), melanoma, pancreatic cancer, glioblastoma, cervical cancer, ovarian cancer, liver cancer, bladder cancer, liver tumor, breast cancer, colon cancer, colorectal cancer, endometrial or uterine cancer, salivary gland cancer, kidney cancer, liver cancer, prostate cancer, vulvar cancer, thyroid cancer, liver cancer, and various types of head and neck cancer, and B-cell lymphoma (including low-grade/follicular non-Hodgkin's lymphoma (NHL); small lymphocyte (SL) NHL; intermediate/follicular NHL; intermediate diffuse NHL; high-grade immunoblastic NHL; high-grade lymphoblastic NHL; high-grade small non-cleaved cell NHL; storage disease NHL; mantle cell lymphoma; AIDS-related lymphoma; and Waldenstrom's macroglobulinemia); chronic lymphocytic leukemia (CLL); acute lymphoblastic leukemia (ALL); hairy cell leukemia; chronic myeloblastic leukemia; and post-transplant lymphoproliferative disorder (PTLD), and abnormal vascular proliferation associated with keloid, edema (such as associated with brain tumors), and Meigs' syndrome.

The following exemplary embodiments are provided to further illustrate the present disclosure. It should be understood that these examples are merely illustrative but not restrictive, and that the present disclosure is limited only by the appended claims.

EXAMPLE

Example 1: Method of Preparing the Compound of the Present Disclosure

As shown in FIG. 1, compounds 2 to 8 were synthesized from commercially available p-bromophenethyl alcohol (compound 1) as the starting compound.

p-Bromophenethyl alcohol (5 mmol, 0.7 ml, compound 1) was dissolved in 50 ml of anhydrous tetrahydrofuran and cooled to −78° C. N-butyllithium/hexane solution (12 mmol, 2.4 eq) was added dropwise, the solution gradually turned yellow and then turned into an off-white paste, which was kept at −78° C. and stirred for 15 min. Then triisopropyl borate (15 mol, 3.5 ml, 3 eq.) was added dropwise, the solution became clear, and the reaction was carried out at −78° C. for 20 min. Then the solution was warmed to room temperature, 50 ml of 10% hydrochloric acid was added, and the mixture was stirred at room temperature for 15 min. The mixture was separated, the aqueous phase was extracted with ethyl acetate (20 ml×3), the organic phases were combined, washed with saturated sodium chloride (30 ml×2), dried over anhydrous sodium sulfate, and the solvent was removed in vacuo to obtain compound 2 (0.66 g, 80%) as a white solid. The compound was directly used in the next reaction without further purification. Compound 2: 1H NMR (400 MHz, Methanol-d4) δ 7.60-6.94 (m, 4H), 3.75 (t, J=7.1 Hz, 2H), 2.82 (t, J=7.1 Hz, 2H).

Compound 2 (0.66 g, 4 mmol) was dissolved in 16 ml of toluene, 1.6 ml of DMSO was added, and then N-methyliminoacetic acid (647 mg, 4.4 mmol, 1.1 eq.) was added. Refluxing was carried out, a water separator filled with toluene was set up, and the reaction was completed after about 2 hours. The organic solvent was removed in vacuo and the product was separated using silica gel column chromatography to obtain compound 3 (650 mg, 59%) as white crystals. Compound 3: 1H NMR (400 MHz, Methanol-d4) δ7.53-7.10 (m, 4H), 4.35-3.96 (m, 4H), 3.75 (t, J=7.0 Hz, 2H), 3.31 (s, 3H), 2.82 (t, J=7.1 Hz, 2H).

Compound 3 (1.1 g, 4 mmol) was dissolved in a mixed solvent of 40 ml of anhydrous dichloromethane and 40 ml of anhydrous tetrahydrofuran, DMP oxidant (1.7 g, 4 mmol, 1 eq.) was added, and then sodium bicarbonate powder (3.36 g, 40 mmol, 10 eq.) was added. The reaction was carried out at room temperature for 1 hour. 40 ml of saturated sodium thiosulfate solution and 40 ml of saturated sodium bicarbonate solution were added and the mixture was stirred for 15 minutes. The insolubles were removed by filtration, the organic phase was separated, the aqueous phase was extracted with ethyl acetate (20 ml×3), the organic phases were combined, washed with saturated sodium chloride (30 ml×2), dried over anhydrous sodium sulfate, and the solvent was removed in vacuo. The product was separated with silica gel column chromatography to obtain compound 4 (541 mg, 49%) as a white solid. Compound 4: 1H NMR (400 MHz, Acetone-d6) δ 9.74 (s, 1H), 7.41 (dd, J=100.7, 7.9 Hz, 4H), 4.48-4.07 (m, 4H), 2.75 (s, 3H).

Compound 4 (541 mg, 1.97 mmol) was dissolved in 20 ml of anhydrous tetrahydrofuran, tert-butylsulfinamide (477 mg, 3.94 mmol, 2 eq.) was added, tetraethyl titanate (3.94 mmol, 840 µl, 2 eq.) was added dropwise, and the mixture was stirred at room temperature for 2 hours. The reaction was quenched by adding 20 ml of water and the mixture was stirred for 10 min, the insolubles were removed by filtration, the organic phase was separated, the aqueous phase was extracted with ethyl acetate (20 ml×3), the organic phases were combined, washed with saturated sodium chloride (30 ml×2), and dried over anhydrous sodium sulfate, and the solvent was removed in vacuo. The product was separated with silica gel column chromatography to obtain compound 5 (490 mg, 66%) as yellow crystals. Compound 5: 1H NMR (400 MHz, Acetone-d6) δ 8.07 (s, 1H), 7.43 (dd, J=83.2, 7.9 Hz, 4H), 4.51-4.03 (m, 4H), 3.91 (d, J=5.1 Hz, 2H), 2.73 (s, 3H), 1.12 (s, 9H).

PCy$_3$·HBF$_4$ (124 mg, 6 mol %) was added to 10 ml of toluene, then CuSO$_4$·5H$_2$O solution (82 mg, 6 mol %) and deionized water (6 mL) were added, and the mixture was stirred vigorously for 10 min at room temperature. Benzylamine (153 µL, 0.25 eq.) was then added under nitrogen and a dark blue catalyst was formed immediately. An additional 50 ml of toluene was added, the reaction system was maintained at 0° C., and compound 5 (2.2 g, 5.7 mmol) and B$_2$pin$_2$ (2.8 g, 2.0 eq.) were added. Subsequently, the reaction system was returned to room temperature, and the reaction was carried out for 1 hour until TLC showed that the reactants were completely consumed. The reaction mixture was washed with saturated EDTA (2×50 mL), and then washed with saturated brine (50 mL). The organic phases were combined and then dried over anhydrous sodium sulfate, and the organic solvent was removed in vacuo to obtain compound 6 (3.0 g) as a yellow oily liquid. The crude product was used directly in the next reaction without purification.

Compound 6 (3.0 g, 5.7 mmol) was dissolved in 50 ml of acetonitrile, 57 ml of 1M NaOH solution was added, and the mixture was stirred at room temperature for half an hour. 4.7 ml of concentrated hydrochloric acid was then added to neutralize the reaction to obtain a reaction mixture containing compound 7, which was directly used in the next reaction.

14.25 ml of 3M KHF$_2$ solution (10 eq.) was added to the reaction mixture containing compound 7, 4.7 ml of concentrated hydrochloric acid was then added dropwise until pH<0, and the reaction was carried out at room temperature for 2 hours. The HCl was removed by evaporation under reduced pressure at 30° C. to reduce the acidity to pH of 2, and the reaction was carried out for 30 min. Acetonitrile was added for azeotropic drying, the solid was washed with acetonitrile, the insolubles were discarded, and the acetonitrile phase was purified using pre-HPLC (phase A: acetonitrile, phase B: water/0.1% TFA, 0-2 min: 5% A, 2-11 min: 5% A to 50% A, the remainder is B) to obtain $BF_3$-BPA (compound 8). The HPLC-MS results are shown in FIG. 2B.

Discussion

The difficulty in the preparation of the compound of the present disclosure lies in that: the removal of the protecting group and the fluorination of the boronic acid group are selectively performed. In this method, N-methyliminoacetic acid (MIDA) is used for the first time to obtain the precursor of $BF_3$-BPA, compound 6, the amino group of which is protected by tert-butylsulfinamide, the α-aminoboronic acid group is protected by boronic acid pinacol ester, and the phenylboronic acid group is protected by MIDA.

compound 6

Figure 4:
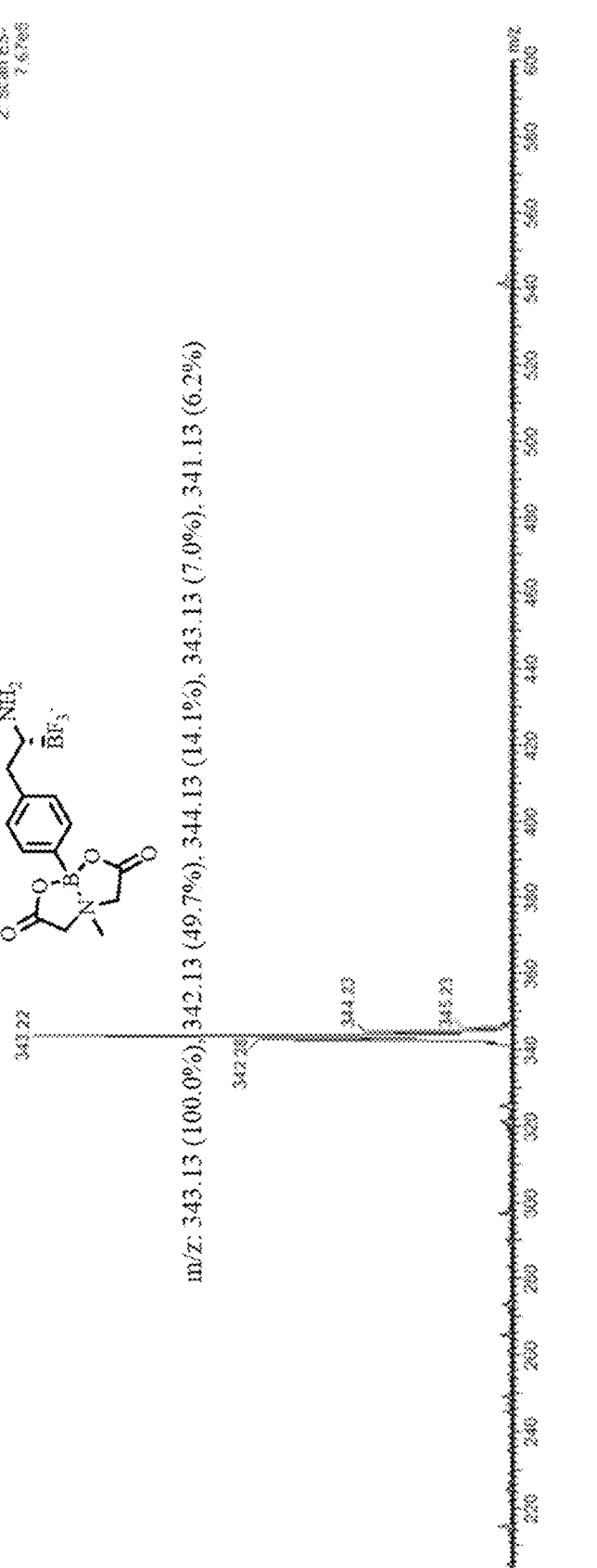
FIG. 4: HPLC-MS [M–H]⁻ mass spectrometry results of compound 9.

The inventors try to use a one-step fluorination method in which 3M $KHF_2$ (10 eq.)/HCl is used to react with compound 6 (pH<0, at room temperature for 2 hours) to directly obtain the target product $BF_3$-BPA. This method finally obtains the boron trifluoride amino acid compound compound 9, the phenylboronic acid group of which is protected by MIDA. FIG. 4 shows the [M–H]⁻ mass spectrometry results of compound 9.

Since phenylboronic acid MIDA needs to be removed by hydrolysis in dilute NaOH solution, compound 7 is hydrolyzed with NaOH aqueous solution to obtain amino-protected compound 10 having double boronic acid groups (FIG. 7). FIG. 5 shows the [M+H]⁺ mass spectrum results of compound 7. However, the duration of the sodium hydroxide hydrolysis should not be too long and the concentration should not be too high (NaOH solution is added to reach a final concentration of 0.4-0.6M, and the mixture is stirred at room temperature for 30 minutes), otherwise phenylboronic acid would be oxidized to phenol and other unpredictable by-products. As shown in the high performance liquid chromatography of FIG. 6 (A phase: acetonitrile, B phase: water/0.1% TFA; 0-2 min: 5% A, 2-15 min: 5% A-100% A, the remainder is B), the phenylboronic acid group is partially oxidized to a phenolic structure.

After the amino-protected compound having double boronic acid groups is obtained, the NaOH used for hydrolysis in the previous step is neutralized by concentrated hydrochloric acid, and then KHF2/HCl is used for fluorination while removing the amino-protecting group. It should be noted that although the preparation of the classic α-aminoboron trifluoride uses a KHF2/HCl solution having a pH of 2, in this example, due to the presence of phenylboronic acid, when pH>0, boron trifluoride compound cannot be obtained, both boron atoms are present in the form of boronic acid groups In order to obtain the target compound, the double-boron trifluoride structure (compound 11, FIG. 8) can only be obtained under the condition of KHF2/HCl having a pH<0. After obtaining the double-boron trifluoride structure, the acidity is reduced by the method of vacuum evaporation to a pH of 2, and finally the target product $BF_3$-BPA can be obtained, indicating that there is a difference in the hydrolysis rate of α-aminoboron trifluoride and aromatic boron trifluoride under this condition, which can be used to prepare the target product $BF_3$-BPA. As shown in FIGS. 2A-2B, the target product $BF_3$-BPA was prepared by the method of the present disclosure (HPLC method, phase A: acetonitrile, phase B: water/0.1% TFA; 20% A, and the remainder is B).

Example 2: Radiochemical Labeling $BF_3$-BPA (compound 8, 250 nmol) was dissolved in 5 μL of DMF, and 5 μl of pyridazine-HCl buffer (1.0 M, pH~2.0) was added, and then ¹⁸F-labeled water-aqueous solution (30 μL, 370 MBq) was added. The reaction mixture was reacted at 85° C. for 15 min, then the reaction was quenched with 0.5 ml of normal saline, and the free fluoride ions were removed with Sep-Pak Alumina Light cartridge to obtain the final product [¹⁸F]$BF_3$-BPA (~55 MBq, RCY 15%). The Radio-HPLC results are shown in FIG. 3 (HPLC method, phase A: acetonitrile, phase B: water/0.1% TFA; 20% A, and the remainder is B).

Example 3: PET Small Animal Imaging

Establishment of tumor model animals: tumor cells (BGC823 human gastric cancer cells and B16-F10 mouse melanoma) were cultivated to an appropriate scale in a 5% $CO_2$ incubator. 4-6 weeks old mice were selected, their right shoulders were shaved, and about $10^6$ tumor cells were suspended in 50 μL of PBS, and injected into the right shoulders of the mice. The mice were raised in a sterile environment for 1-2 weeks when the tumor volume reached a specific volume, and the tumor model was established.

200 μCi of labeled compound $[^{18}F]BF_3$-BPA was dissolved in 0.15 ml of normal saline, and injected into the mouse with the tumor implanted in the shoulder through tail vein injection, and 1 hour after the injection, PET/CT acquisition was carried out for 15 minutes and image reconstruction was made, and the results are shown in FIG. 9. It is shown that $[^{18}F]BF_3$-BPA was highly enriched in the tumor site, and showed clear contrast on imaging, which shows that it can be used for tumor diagnosis and achieve good results.

Example 4: Boron Neutron Capture Therapy Experiment

BPA, $BF_3$-BPA and $BF_3$-Phe containing natural boron were dissolved in normal saline at a dose of 500 mg/kg, and injected into the above-mentioned mouse with the tumor planted in the shoulder through the tail vein, and BNCT treatment was performed at 1 hour, the tumor size was measured in the following 21 days and compared with the mouse of the group injected with BPA, $BF_3$-Phe and underwent neutron beam irradiation alone.

As shown in FIG. 10, the use of $BF_3$-BPA combined with neutron beam for BNCT can achieve excellent tumor suppression effect and is an excellent BNCT drug. In the BNCT comparison test, the effects of the BNCT experiments using classic BNCT drug BPA, the boron-containing amino acid $BF_3$-Phe developed based on the boron trifluoride strategy, and the $BF_3$-BPA of the present application under the same conditions were compared. As can be seen, because $BF_3$-BPA contains two boron atoms in its molecular structure, $BF_3$-BPA has higher boron delivery efficiency than BPA and $BF_3$-Phe which have only one boron atom in their molecular structures under the same experimental conditions, so $BF_3$-BPA can effectively improve the efficacy of BNCT. This is of great significance for shortening the treatment period, reducing the dosage of drugs, reducing the radiation dose and patient expenses, and reducing complications and side effects.

While the invention has been described with reference to specific embodiments thereof, it will be understood by those skilled in the art that various changes may be made and equivalents may be used instead without departing from the spirit and scope of the invention. In addition, many modifications may be made to adapt a particular situation, material, composition, method, method step or steps to the purpose, spirit and scope of the invention. All such modifications are intended to be within the scope of the appended claims.

What is claimed:

1. A compound of Formula I:

Formula I wherein, R group is hydrogen, alkyl, or methyl.

2. The compound according to claim 1, wherein:

the boron atom attached to the benzene ring is $^{10}B$ or natural boron, at least one of the fluorine atoms in $—BF_3^-$ is radiolabeled; and the boron atom in $—BF_3^-$ is natural boron.

3. A composition of a boron-carrying agent comprising the compound according to claim 1 and a pharmaceutically acceptable carrier.

4. The composition of the boron-carrying agent according to claim 3, further comprising a component selected from the group consisting of fructose, disodium mercaptoundecahydrododecaborate and dimers thereof, boronated dendrimer-EGF bioconjugates, EGFR monoclonal antibody-borate conjugates, FR-targeted boron-containing liposomes, FR-targeted boron-containing nanoparticles, and borate porphyrins.

5. A method of preparing the compound according to claim 1 the method, comprising steps of:

producing an intermediate containing double boron trifluoride groups by adding $KHF_2$ solution to compound 7 and adding hydrochloric acid to reach an acidity of pH<0; and increasing the acidity to a pH of 1.5 to 4 to obtain the compound according to claim 1.

6. The method according to claim 5, wherein compound 7 is obtained by:

adding NaOH solution to compound 6

6 to achieve a final concentration of 0.4-0.6 M, stirring the solution at room temperature for 20-40 minutes, and adding concentrated hydrochloric acid for neutralization.

7. The method according to claim 5, further comprising obtaining compound 3

3 by adding N-methyliminoacetic acid to compound 2

8. The method according to claim 5, further comprising:

1

(1) converting p-bromobenzene ethanol to compound 2

(2) converting compound 2 to compound 3

3 with the addition of N-methyliminoacetic acid;

(3) converting compound 3 to compound 4

4

(4) converting compound 4 to compound 5

5

(5) converting compound 5 to compound 6

6

(6) converting compound 7 to compound 8

8(BF$_3$-BPA)

and (7) converting compound 8 to

[$^{18}$F]BF$_3$-BPA

9. A method of treating or diagnosing cancer using the boron-carrying compound according to claim 1.

10. The method according to claim 9, wherein the medicament is a boron-carrying agent for integrated tumor diagnosis and treatment or boron neutron capture therapy.

11. The method according to claim 9, wherein the cancer is at least one of squamous cell carcinoma, lung cancer, peritoneal cancer, hepatocellular carcinoma, gastric cancer, pancreatic cancer, melanoma, glioblastoma, cervical cancer, ovarian cancer, liver cancer, bladder cancer, hepatic tumor, breast cancer, colon cancer, colorectal cancer, uterine cancer, salivary gland cancer, kidney cancer, prostate cancer, vulvar cancer, thyroid cancer, head and neck cancer, B-cell lymphoma, or leukemia.

12. A method of treating or diagnosing cancer using the boron-carrying agent according to claim 3.

13. The method according to claim 12, wherein the boron-carrying agent is for integrated tumor diagnosis and treatment or boron neutron capture therapy.

14. The method according to claim 12, wherein the cancer is at least one of squamous cell carcinoma, lung cancer, peritoneal cancer, hepatocellular carcinoma, gastric cancer, pancreatic cancer, melanoma, glioblastoma, cervical cancer, ovarian cancer, liver cancer, bladder cancer, hepatic tumor, breast cancer, colon cancer, colorectal cancer, uterine cancer, salivary gland cancer, kidney cancer, prostate cancer, vulvar cancer, thyroid cancer, head and neck cancer, B-cell lymphoma, or leukemia.

* * * * *